United States Patent [19]

Brantl

[11] Patent Number: 5,030,630
[45] Date of Patent: * Jul. 9, 1991

[54] USE OF 6-ALLYL-2-AMINO-5,6,7,8-TETRAHYDRO-4H-THIAZOLO[5,4,-D]AZEPINE-FOR TREATING DISEASES CAUSED BY REDUCED SECRETION OF GROWTH HORMONE

[75] Inventor: Victor Brantl, Frauenplatz, Fed. Rep. of Germany

[73] Assignee: Boehringer Ingelheim KG, Ingelheim am Rhein, Fed. Rep. of Germany

[ * ] Notice: The portion of the term of this patent subsequent to Jul. 25, 2006 has been disclaimed.

[21] Appl. No.: 338,690

[22] Filed: Apr. 17, 1989

Related U.S. Application Data

[62] Division of Ser. No. 130,909, Dec. 10, 1987, Pat. No. 4,851,408.

[30] Foreign Application Priority Data

Dec. 13, 1986 [DE] Fed. Rep. of Germany ....... 3642648

[51] Int. Cl.$^5$ .............................................. A61K 31/55
[52] U.S. Cl. .................................................... 514/215
[58] Field of Search ........................................ 514/215

[56] References Cited

U.S. PATENT DOCUMENTS 3,907,996  9/1975  Griss et al. ........................... 514/215
4,400,378  8/1983  Innemee et al. ..................... 514/215
4,851,408  7/1989  Brantl .................................. 514/215

Primary Examiner—Frederick E. Waddell
Assistant Examiner—Raymond J. Henley, III
Attorney, Agent, or Firm—D. E. Frankhouser; M-E. M. Timbers; A. R. Stempel

[57] ABSTRACT

The use of 6-allyl-2-amino-5,6,7,8-tetrahydro-4H-thiazolo[4,5-d]azepine and pharmacological acid addition salts thereof for the release of growth hormone.

1 Claim, No Drawings

USE OF 6-ALLYL-2-AMINO-5,6,7,8-TETRAHYDRO-4H-THIAZOLO[5,4,-D]AZEPINE-FOR TREATING DISEASES CAUSED BY REDUCED SECRETION OF GROWTH HORMONE

This is a division of application Ser. No. 130,909, filed Dec. 10, 1987, now U.S. Pat. No. 4,851,408.

The invention relates to the use of a thiazoloazepine derivative and the pharmacologically acceptable acid addition salts thereof for the release of growth hormone, e.g. for treating growth disorders.

German Offenlegungsschrift No. 20 40 510 describes thiazolo-and oxazolo-derivatives of general formula

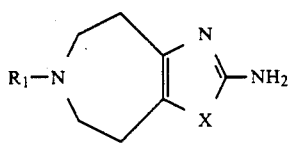

wherein $R_1$ represents a hydrogen atom, an alkyl group with 1 to 4 carbon atoms optionally substituted by a hydroxyl group, a benzoyl group optionally substituted by a halogen atom or by a methyl or methoxy group, or an allyl group and X represents an oxygen or sulphur atom, and the physiologically acceptable acid addition salts thereof with inorganic or organic acids.

It is also known from this Offenlegungsschrift that the compounds of general formula I have valuable pharmacological properties; the specification describes both antitussive and hypotensive properties, depending on X. A delayed-release form for the oral treatment of hypertension and angina pectoris is disclosed in DE-OS 28 36 387. U.S. Pat. No. 4 400 378 also describes an antiglaucoma property of compounds of general formula I.

Moreover, 6-allyl-2-2-amino-5,6,7,8-tetrahydro-4H-thiazolo[4,5-d]azepine is described in numerous scientific publications under the name B-HT 920. Applications relating to a second medical indication were filed in the form of DE-OS 35 02 365, relating to a composition for lowering the prolactin serum level, and in DE-OS 35 03 963, concerning a composition for the treatment of Parkinsonism. Compounds which bring about the release of growth factor are already known from numerous publications and patent applications (Bibl.: F. X. Coude et al., Trends in Biotechnology 1984, Volume 2, page 83 ff; M. O. Thorner in "The Lancet", July 16, 1983, page 119 ff; EP-OS 0 136 475) These are polypeptides, generally with a sequence of 40 amino acids. In the English-language publications, these peptides are also referred to as "Growth Hormone Releasing Factor" (GRF). These compounds may be prepared by conventional chemical synthesis or also by genetic engineering. Owing to the complex structure of these peptides it has hitherto not been possible to produce them in large quantities by conventional synthesis and even genetic engineering does not produce them any more cheaply on a larger scale.

Surprisingly, it has been found that B-HT 920 causes the release of growth hormone in humans. BH-T 920 and the physiologically acceptable acid addition salts thereof are suitable for preparing a drug for the treatment of growth disorders. It may be used to treat diseases which are based on a reduced secretion of growth hormone, e.g. growth disorders in children such as restricted growth, and also in reduced metabolism, e.g. malnutrition, cachexia caused by tumours or chemotherapy; chronic anoxaemia caused by respiratory insufficiency or cardiopathy, kidney failure. Other indications include bone fractures, burns, wound healing and the acceleration of blood production.

For diagnostic purPoses, B-HT 920 can be used to stimulate the release of growth hormone and thus determine whether there is sufficient growth hormone in the hypophysis.

For the release of growth hormone, B-HT 920 and the acceptable acid addition salts thereof (e.g. B-HT 920 $Cl_2$) may be incorporated in the conventional galenic preparations for oral, rectal, parenteral or transdermal use.

The single dose by oral route for humans is normally between 0.05 mg and 0.3 mg, preferably 0.1 to 0.25 mg. When administered several times throughout the day the total dosage may be between 0.6 and 1.0 mg.

The following are clinical trials investigating the release of growth hormone by B-HT 920 $Cl_2$.

The tests are carried out with six male subjects ranging in age from 21 to 46. Each subject was given 0.15 to 0.2 mg of B-HT 920 $Cl_2$ in tablet form.

The measurement of the growth hormone in the serum was carried out using a standard radioimmunological process.

The serum levels were determined before and after administration. The blood samples were taken through a fixed vein cannula which was put into position 1 hour before administration of the substance and determination of the 0 level. The measurements obtained are listed in Table I. They are given in ng/ml.

| Dosage B-HT920Cl$_2$ | Test subject | 0 level t = 0 | Hours after medication | | | | |
|---|---|---|---|---|---|---|---|
| | | | 1 | 2 | 3 | 5 | 8 |
| 0.15 mg | 1 | 0.3 | 0.5 | 0.3 | 3.5 | 4.4 | 0.4 |
| 0.15 mg | 2 | 0.4 | 0.3 | 0.3 | 0.5 | 3.3 | 0.3 |
| 0.20 mg | 3 | 1.5 | 0.4 | 2.5 | 9.5 | 1.0 | 0.5 |
| 0.15 mg | 4 | 0.3 | 0.32 | 1.7 | 0.3 | 0.2 | 0.2 |
| 0.15 mg | 5 | 0.3 | 7.3 | 0.6 | 0.4 | 0.2 | 0.3 |
| 0.15 mg | 6 | 0.4 | 20.0 | 12.4 | 1.4 | 0.4 | 0.4 |

The substance is very well tolerated and no undesirable effects such as dryness of the mouth, fatigue or dizziness are experienced.

The following Examples describe the preparation of some pharmaceutical forms:

EXAMPLE I

Coated tablet core

| Composition: 1 tablet core contains | |
|---|---|
| B-HT 920 Cl$_2$ | 100 μg |
| Lactose | 38.45 mg |
| Corn starch | 10.0 mg |
| Gelatine | 1.0 mg |
| Magnesium stearate | 0.5 mg |

Method

The mixture of the active substance with lactose and corn starch is granulated with a 10% aqueous gelatine solution by passing through a 1 mm screen, dried at 40° C. and passed through the same screen again. The granules thus obtained are mixed with magnesium stearate and compressed to form tablet cores. This procedure should be carried out in a darkened room.

| | |
|---|---|
| Weight of core: | 50 mg |
| Punch: | 5 mm, convex |

The tablet core thus obtained are coated in known manner with a coating consisting essentially of sugar and talc. The finished coated tablets are polished with beeswax.

| | |
|---|---|
| Weight of coated tablet: | 100 mg |

EXAMPLE II

Suppositories

| 1 suppository contains | |
|---|---|
| B-HT 920 Cl$_2$ | 100.0 μg |
| Suppository mass (e.g. Witepsol W 45) | 1690.0 mg |

Method

The finely powdered substance is stirred, by means of an immersion homogenizer, into the molten suppository mass which has been cooled to 40° C. At 35° C. the mass is poured into slightly chilled moulds.

EXAMPLE III

Ampoules containing 200 mcg of B-HT 920

| 1 ampoule contains: | |
|---|---|
| B-HT 920 | 200 μg |
| Citric acid | 7.0 mg |
| Sec. sodium phosphate 2H$_2$O | 3.0 mg |
| Sodium phyrosulphite | 1.0 mg |
| Distilled water ad | 1.0 ml |

Method

The buffer substances, active substance and sodium pyrosulphite are dissolved successively in the distilled water which has been cooled under a current of CO$_2$. The solution is made up to the specified volume with distilled water and filtered to remove any pyrogens.

Packaging: in brown ampoules under protective gas
Sterilization: 20 minutes at 120° C.

The ampoule solution must be prepared and packaged in a darkened room.

EXAMPLE IV

Coated tablets containing 0.1 mg of B-HT 920 Cl$_2$

| 1 tablet core contains: | |
|---|---|
| B-HT 920 Cl$_2$ | 100 μg |

| -continued | |
|---|---|
| 1 tablet core contains: | |
| Lactose | 36.0 mg |
| Corn starch | 12.4 mg |
| Gelatine | 1.0 mg |
| Magnesium stearate | 0.5 mg |

Method

| Analogously to Example I | |
|---|---|
| Weight of core | 50 mg |
| Punch: | 5 mm, convex |
| Weight of coated tablet: | 100 mg |

EXAMPLE V

Gelatine capsules containing 250 mcg of B-HT 920 Cl$_2$

| 1 capsule contains: | |
|---|---|
| B-HT 920 Cl$_2$ | 250 μg |
| Corn starch | 85.7 mg |

Method

The substances are intensively mixed and packed into opaque capsules of suitable size.

Example of preparation of a transdermal form

| Composition: |
|---|
| 9.744 g of Eudragit ® E 30 D (Messrs. Rohm, Darmstadt) |
| 0.600 g of Eudragit ® E 100 (Messrs. Rohm, Darmstadt) |
| 1.656 g of B-HT 920 Cl$_2$ |
| 12.000 g solids |
| 6.000 g acetone |
| 22.000 g methanol |
| 100.000 g solution |

The Eudragit ® E 100 is previously dissolved in acetone, then the Eudragit ® E 30 D and half the methanol are added and the mixture is stirred. When a homogeneous solution has been formed, the active substance and the remaining methanol are added in batches. The resulting solution is poured onto a film drawing apparatus (made by Erichsen) onto a PrePared backing layer impervious to the active substance and spread with a doctor blade at a position of 0.6 mm. After 10 minutes' drying a second and then a third layer are applied with the doctor blade in the same position. After drying, a film is obtained in a thickness of 100 microns. The film is then packaged and, for use, is attached to the skin by means of a suitable sticking plaster.

What is claimed is:

1. A method of treating disease in a warm-blooded animal caused by reduced secretion of growth hormone which comprises administering to said animal a growth-hormone-releasing amount of 6-allyl-2-amino-5,6,7,8-tetrahydro-4H-triazolo-[5,4-d]azepine or the pharmacologically acceptable acid addition salts thereof.

* * * * *